(12) United States Patent
Hansen

(10) Patent No.: US 11,402,080 B2
(45) Date of Patent: Aug. 2, 2022

(54) DYNAMIC ILLUMINATION USING A COHERENT LIGHT SOURCE

(71) Applicant: KORRUS, INC., Los Angeles, CA (US)

(72) Inventor: Monica Hansen, Los Angeles, CA (US)

(73) Assignee: KORRUS, Inc., Los Angeles, CA (US)

( * ) Notice: Subject to any disclaimer, the term of this patent is extended or adjusted under 35 U.S.C. 154(b) by 0 days.

(21) Appl. No.: 16/883,938

(22) Filed: May 26, 2020

(65) Prior Publication Data
US 2020/0370730 A1 Nov. 26, 2020

Related U.S. Application Data

(60) Provisional application No. 62/852,222, filed on May 23, 2019, provisional application No. 62/852,218, filed on May 23, 2019.

(51) Int. Cl.
| | |
|---|---|
| F21V 14/06 | (2006.01) |
| G02B 26/08 | (2006.01) |
| F21V 3/00 | (2015.01) |
| A61L 2/10 | (2006.01) |
| A61L 2/26 | (2006.01) |
| A61L 2/08 | (2006.01) |
| F21Y 115/30 | (2016.01) |
| A61B 1/07 | (2006.01) |
| A61N 5/06 | (2006.01) |

(52) U.S. Cl.
CPC .............. *F21V 14/06* (2013.01); *A61L 2/084* (2013.01); *A61L 2/10* (2013.01); *A61L 2/26* (2013.01); *F21V 3/00* (2013.01); *G02B 26/0875* (2013.01); *A61B 1/07* (2013.01); *A61L 2202/11* (2013.01); *A61N 5/0618* (2013.01); *F21Y 2115/30* (2016.08)

(58) Field of Classification Search
CPC ........ F21V 14/06; F21V 3/00; G02B 26/0875; F21Y 2115/30
See application file for complete search history.

(56) References Cited

U.S. PATENT DOCUMENTS

| | | | |
|---|---|---|---|
| 2009/0190131 A1* | 7/2009 | Gollier | G02F 1/377 356/400 |
| 2011/0141754 A1* | 6/2011 | Hikmet | F21S 41/16 362/509 |
| 2013/0258689 A1* | 10/2013 | Takahira | F21S 41/176 362/465 |
| 2013/0314937 A1* | 11/2013 | Takahashi | F21S 41/16 362/538 |

(Continued)

FOREIGN PATENT DOCUMENTS

| | | | | |
|---|---|---|---|---|
| EP | 3135988 A1 | * | 3/2017 | ............ F21S 41/16 |
| WO | WO-2016035435 A1 | * | 3/2016 | ............ B60Q 1/04 |

*Primary Examiner* — Donald L Raleigh
(74) *Attorney, Agent, or Firm* — FisherBroyles LLP

(57) ABSTRACT

An illumination source, comprising: (a) at least one coherent light emitting device (CLED) configured for emitting coherent light having an optical path; (b) at least one optical element in said optical path for converting at least a portion of said coherent light to incoherent light, said optical element being configured to emit said incoherent light in a direction; and (c) a light control mechanism (LCM) for altering said direction of said incoherent light.

6 Claims, 11 Drawing Sheets

(56) References Cited

U.S. PATENT DOCUMENTS

2014/0321151 A1* 10/2014 Sato .................... H01S 5/02284
                                                            362/553
2018/0255622 A1*  9/2018 Spero ..................... F21S 41/153
2018/0292644 A1* 10/2018 Kamali ................... G02B 1/002
2019/0301700 A1* 10/2019 Yamazumi ............ F21S 41/657
2019/0323663 A1* 10/2019 Rudy ...................... H01S 5/005

* cited by examiner

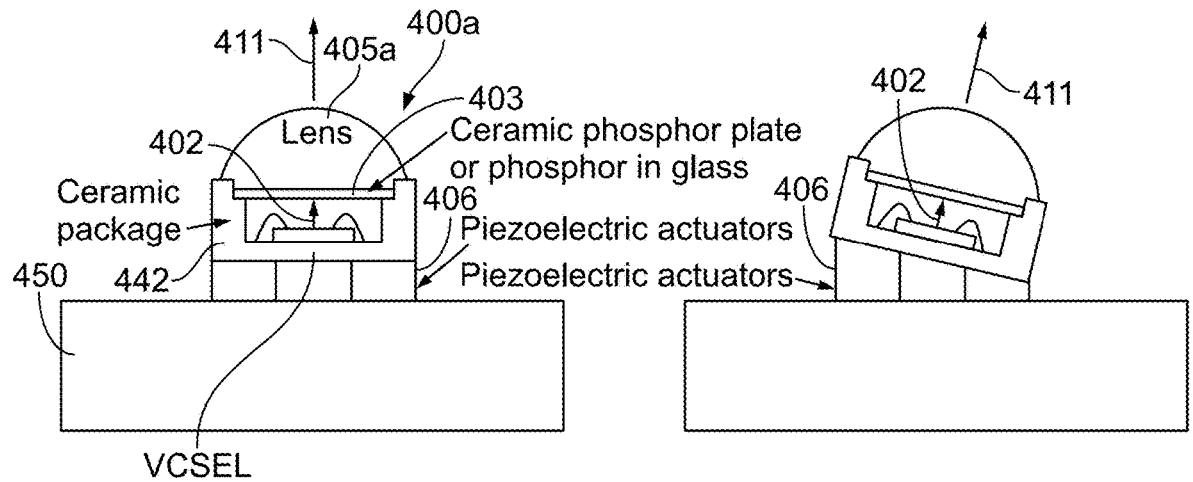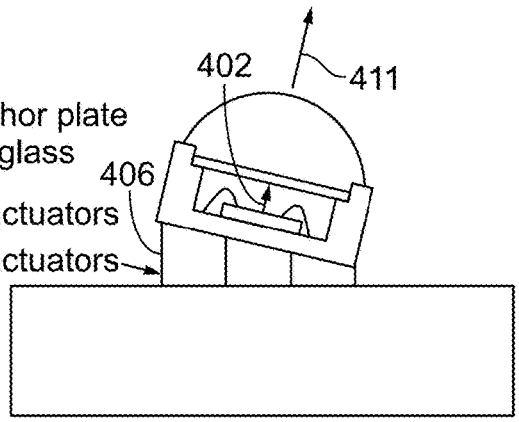
FIG. 4A  FIG. 4B
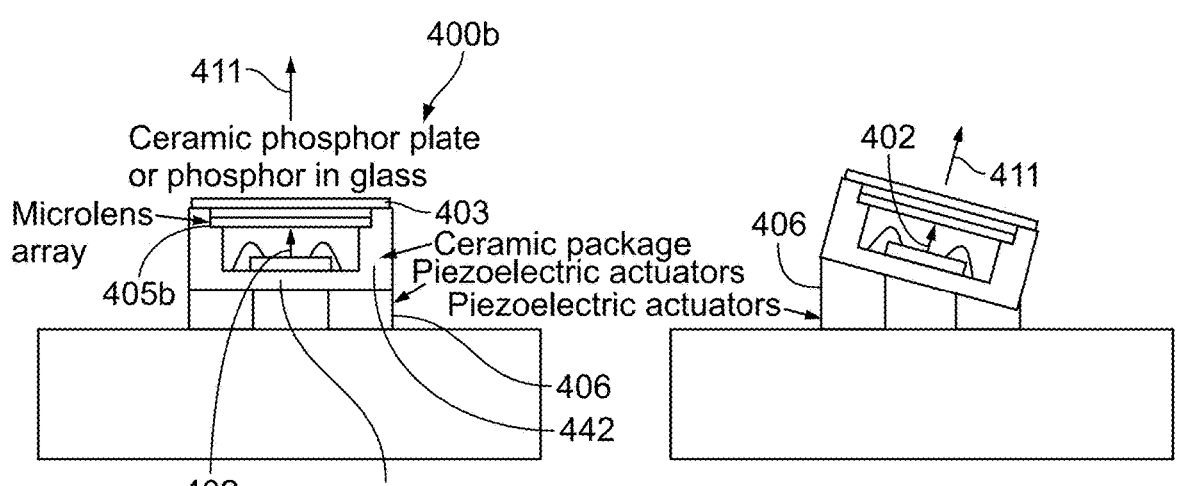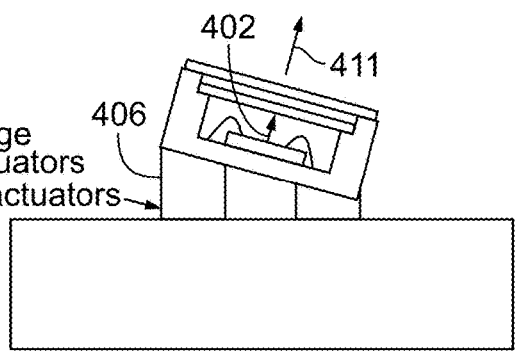
FIG. 4C  FIG. 4D
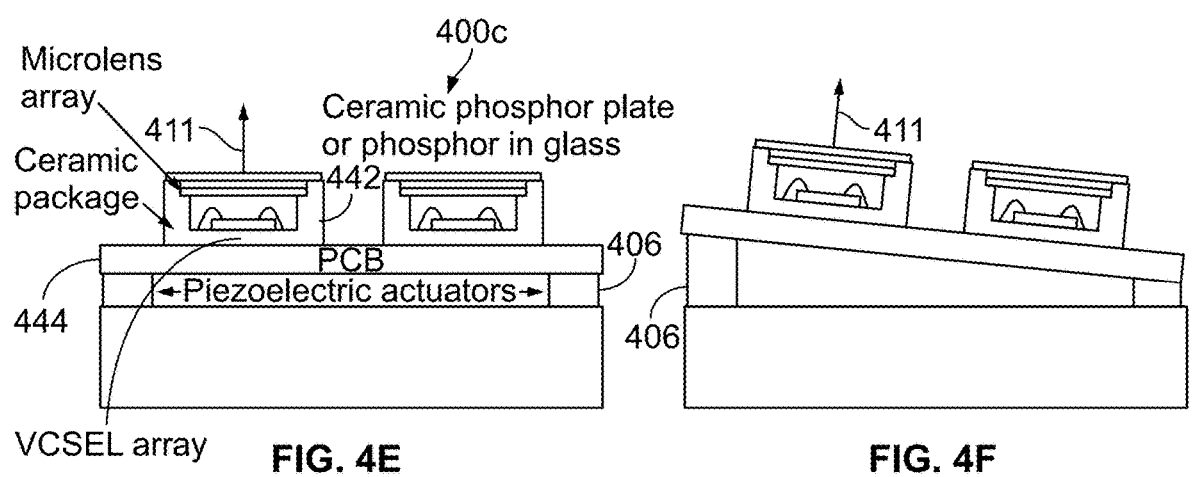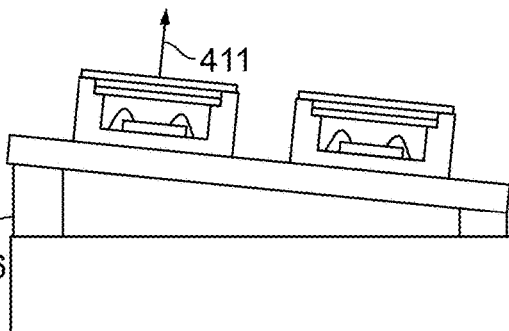
FIG. 4E  FIG. 4F

DYNAMIC ILLUMINATION USING A COHERENT LIGHT SOURCE

REFERENCE TO RELATED APPLICATIONS

This application claims priority to U.S. Provisional Application No. 62/852,222, filed on May 23, 2019, and U.S. Provisional Application No. 62/852,218, filed on May 23, 2019, both of which are incorporated herein by reference in their entirety including their appendices

FIELD OF DISCLOSURE

This disclosure relates generally to using coherent light devices, such as lasers, in illumination sources, and more specifically to dynamically controlling coherent light sources to adjust the direction, shape, and/or quality of the emitted light of illumination sources.

BACKGROUND

Light emitting diodes (LEDs) have become a popular choice for lighting applications. LED lamps are significantly brighter, more efficient, and have a lifespan much longer than incandescent lamps. Although LEDs have significant benefits over traditional incandescent light sources, Applicant recognizes that a light source having a smaller beam of spatially coherent light, such as laser, may provide improved efficiency over LEDs in some illumination applications, such as spot lighting and linear accents. In addition, the smaller source size of the laser can lead to improved dynamic optical control and enable applications such as entertainment lighting and way finding. Moreover, as the cost of lasers, particularly for vertical cavity surface emitting lasers (VCSELs), continues to drop, their appeal in lighting applications increases.

While the smaller beam and source size of lasers may be beneficial, coherent light emitted from lasers also presents challenges. Specifically, coherent light is not only monochromatic, but also potentially hazardous to eyes/retina and other tissues. For this and other reasons, the adoption of lasers in commercial and residential lighting applications is still in its infancy.

Applicant recognizes the need for a dynamic illumination using coherent light while avoiding the hazards of coherent light. The present invention fulfills this need among others.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Applicant recognizes that while coherent light presents challenges in connection with its monochromicity and its potential hazard to eyes/retina, it also presents an enhanced ability to control the direction, shape and quality of the emitted light compared to incoherent light sources. For example, in one embodiment, the direction of the incoherent emitted light is controlled by controlling the direction of the coherent light. In another embodiment, the outputs of different wavelength coherent light sources are combined and balanced to achieve desired spectrums for white light, circadian-friendly lighting, and/or antibacterial lighting, just to name a few.

In one embodiment, an illumination source comprises: (a) at least one coherent light emitting device (CLED) configured for emitting coherent light having an optical path; (b) at least one optical element in the optical path for converting at least a portion of the coherent light to incoherent light, the optical element being configured to emit the incoherent light in a direction; and (c) a light control mechanism (LCM) for altering the direction of the incoherent light.

In another embodiment, an illumination source comprises: (a) an array of coherent light emitting devices (CLEDs), each CLED configured for emitting coherent light having an optical path, at least two or more of CLEDs configured for emitting coherent light having different wavelengths, wherein the array of CLEDs comprises separately controllable drivers controlled by a control signal such that the output of at least a portion of the array of CLEDs is variable based on the control signal; and (b) at least one optical element in the optical path for converting at least a portion of the coherent light to incoherent light.

BRIEF DESCRIPTION OF FIGURES

FIGS. 4A-4F show different embodiments of the actuators used in the LCM of the present invention.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figure 1A:
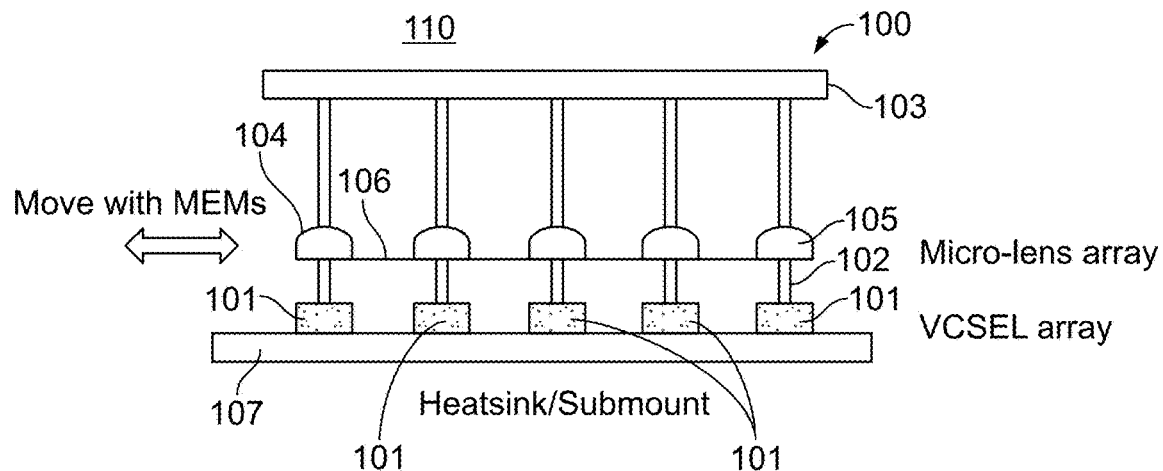
FIG. 1A shows one embodiment of the illumination source of the present invention having an array of CLEDs of the same wavelength with movable lenses in the optical path of the coherent light to alter the direction of emitted incoherent light.
Figure 1B:
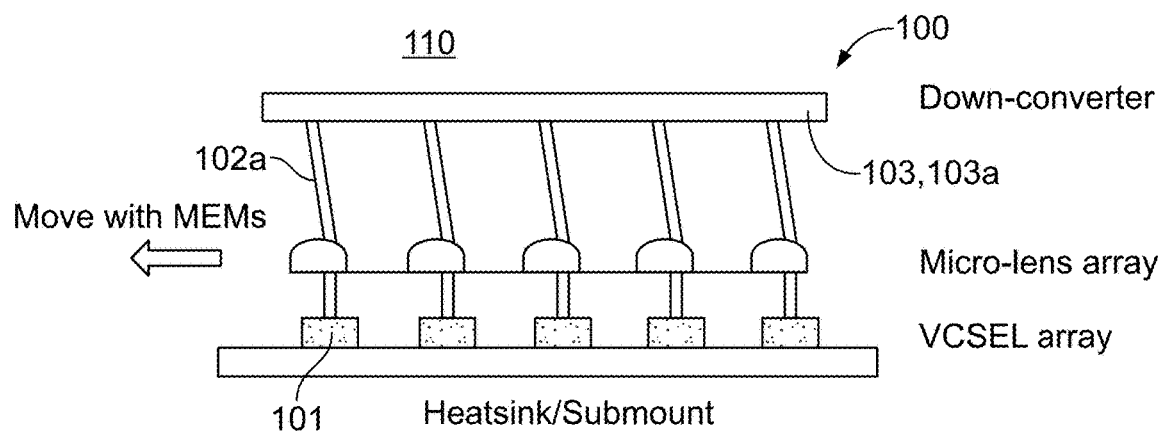
FIG. 1B shows the embodiment of FIG. 1A with the lenses shifted to change the direction of the emitted incoherent light.

Referring to FIGS. 1A and 1B, one embodiment of an illumination source 100 of the present invention is shown. In this embodiment, the illumination source 100 comprises at least one coherent light emitting device (CLED) 101 configured for emitting coherent light 102 having an optical path. At least one optical element 103 is disposed in the optical path for converting at least a portion of the coherent light to incoherent light 110, the optical element being configured to emit the incoherent light in a direction. The illumination source also comprises a light control mechanism (LCM) 104 for altering the direction of the incoherent light. As used herein, the term "coherent light" refers to light that has either temporal or spatial coherence, and the term "incoherent light" refers to light that has neither temporal nor spatial coherence.

Figure 2:
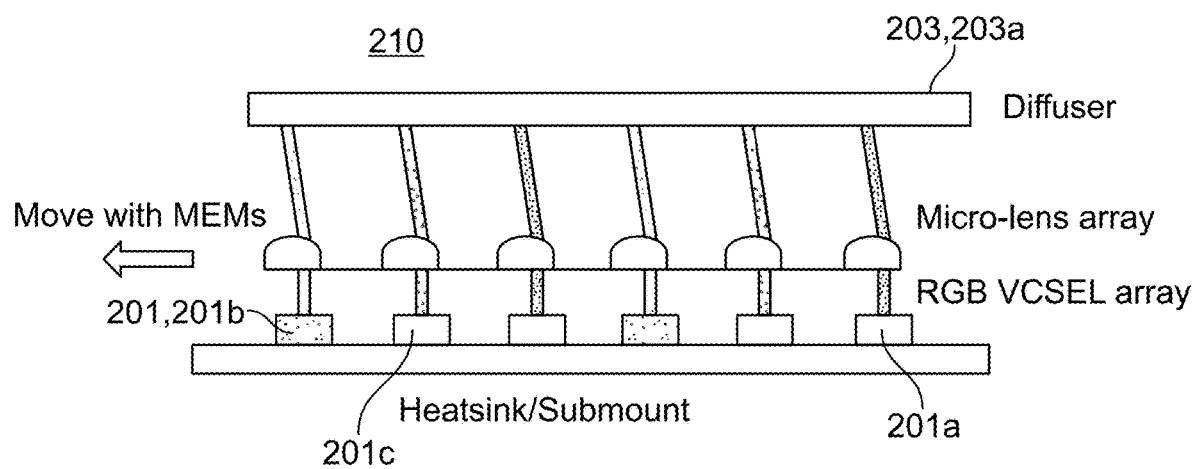
FIG. 2 shows an embodiment of the illumination source, similar to that of FIG. 1A, but with CLEDs of different wavelengths.

Referring to FIG. 2, another embodiment of an illumination source 200 of the present invention is shown. In this embodiment, the illumination source 200 comprises an array of CLEDs 201, each CLED configured for emitting coherent light having an optical path, at least two or more of CLEDs 201a, 201b, 201c, configured for emitting coherent light having different wavelengths. The array of CLEDs also comprises separately controllable drivers (not shown) controlled by a control signal such that the coherent light output 202a, 202b, 202c of at least a portion of the array of CLEDs 201a, 201b, 201c is variable based on the control signal. At least one optical element 203 is disposed on the optical path of the coherent light output for converting at least a portion of the coherent light to incoherent light 210.

These elements are described below in greater detail and in the context of selected alternative embodiments.

LCM

The LCM functions to change either the direction and/or the shape of the incoherent light being emitted from the illumination source. The LCM has various embodiments that function to change the direction and/or shape of the incoherent light in different ways. For example, in one embodiment, the LCM changes the direction of the incoherent light by bending the coherent light. Alternatively, rather than bending the coherent light, the LCM moves the CLED to change the optical path of the coherent light. In still another embodiment, the LCM alters the direction of the incoherent light by bending the incoherent light as it leaves the optical element. These different approaches are described in detail below in connection with various configurations of the LCM. Still other embodiments of the LCM will be obvious to those of skill in the art in light of this disclosure.

Referring to FIGS. 1A and 1B, one embodiment of the LCM 104 is shown in which the optical path 102 of the coherent light from the CLED 101 is bent. In this embodiment, the LCM comprises at least one second optical element 105 in the optical path before the optical element 103, and an actuator 106 operatively connected to the second optical element to change at least one characteristic of the second optical element in response to a control signal, wherein changing the characteristic causes the optical path to change such that the incoherent light being emitted from the optical element changes its direction.

In this particular embodiment, the second optical element 105 is at least one lens, and the actuator 105 changes a position characteristic of the lens relative the CLED. The lens may be a discrete lens optically coupled with a discrete CLED, or it may be an array of lenses optically coupled to an array of CLEDs. Such lenses and their fabrication techniques are well-known in the art. For example, in one embodiment, cyclic olefin copolymer (COC) may be used if the lenses are molded, and benzocyclobutene (BCB) may be used if the lenses are prepared using lithographic patterning.

In one embodiment, changing the position characteristic comprises moving the lens laterally with respect to the axis of the optical path as shown in FIG. 1B. As the lenses are moved laterally, the optical path 102a is bent causing its angle of incidence upon the optical element 103 to change. This change thereby affects the direction of the incoherent light emitted from the optical element 103.

Alternatively, rather than actuating the lenses laterally with respect to the optical axis, the lenses may be actuated axially with respect to the optical axis, or they may be tilted on their z axis (optical axis). Still other approaches for actuating the lenses will be known to those of skill in the art in light of this disclosure.

Figure 6:
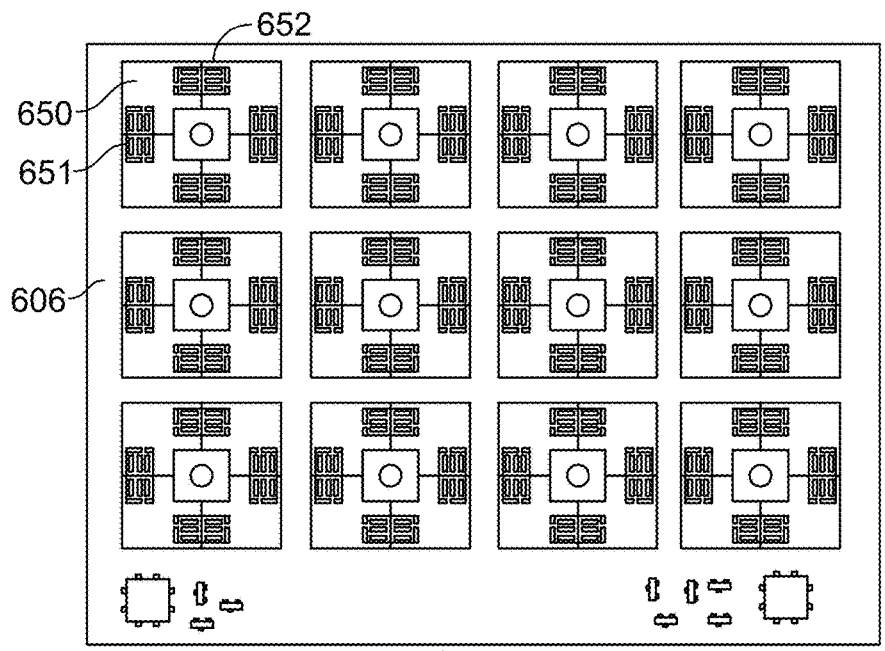
FIG. 6 shows one embodiment of a MEMS for altering the position of the lenses.

In one embodiment, the actuator 106 functions to move one or more lenses to affect the optical path of either the coherent light or the incoherent light, or both. The actuator may have various embodiments, including those based on micro-electromechanical system (MEMS) positioning systems, piezoelectric actuators, and even manual actuators. For example, referring to FIG. 6, one embodiment of the actuator 606 is shown comprising a MEMS positioning system. This particular MEMs is a comb drive (electrostatic) MEMS, which is well suited for x/y translation. In another embodiment, in which the movement of the lens is not in the xy-direction, but instead, for example, involves tipping/tilting the lens along the optical axis, then another MEMS, such as bimporph (electrothermal) actuator, may be preferable.

Referring back to FIG. 6, the MEMS embodiment of FIG. 6 is a 4×3 array of MEM elements. In this embodiment, each MEM element 650 comprises one set of x-direction electromechanical actuators 651 and one set of y-direction electromechanical actuators 652. Although this LCM embodiment is configured as a 4×3 array, other embodiments are possible including a single element MEM or arrays of any number. It should be noted that the driving circuitry for driving the MEMS in the XY direction is not shown, but is well known to those of skill in the art.

Figure 8:
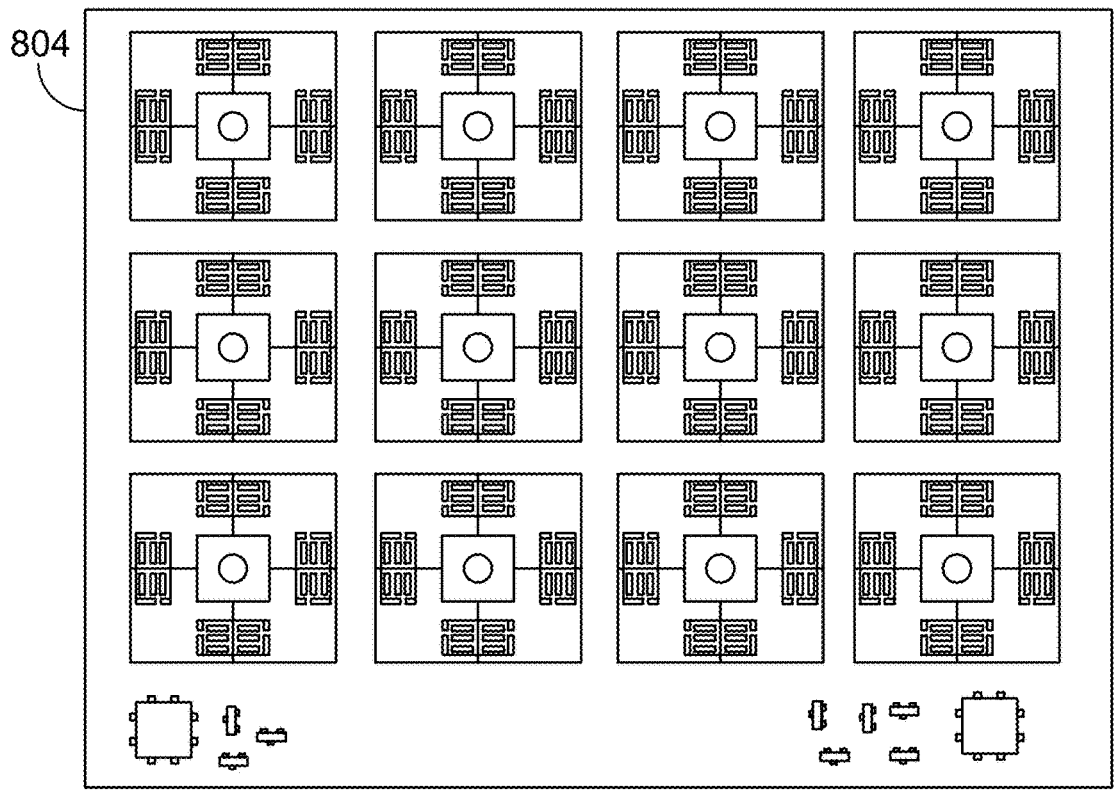
FIG. 8 shows the combination of the MEMS of FIG. 6 and the array of phosphors of FIG. 7.

In one embodiment of the LCM of FIG. 8, the MEMS facilitates the independent movement of each lens in an array of lenses. In other words, each lens 750 of the array of lenses 705 may correspond to a separately controllable MEMS element 650, such that the movement of each lens can be controlled discretely. Alternatively, rather than actuating lenses individually, the entire array may be moved as a unit. For example, referring to FIGS. 3A-3C, various embodiments are shown in which the entire lens assembly is moved rather than discrete lenses within an array. For example, referring to FIG. 3, one embodiment of the illumination source 300a is shown, comprising a ceramic package 331 in which is mounted a CLED 301a. The ceramic package 331 is mounted on a PCB or submount or heatsink 330 as shown. This ceramic package 331 comprises walls upon which MEMS 306 are mounted. Attached to the MEMS 306 is a lens 305a as shown. In this embodiment, a single lens is moved using the MEMS.

Figure 3A:
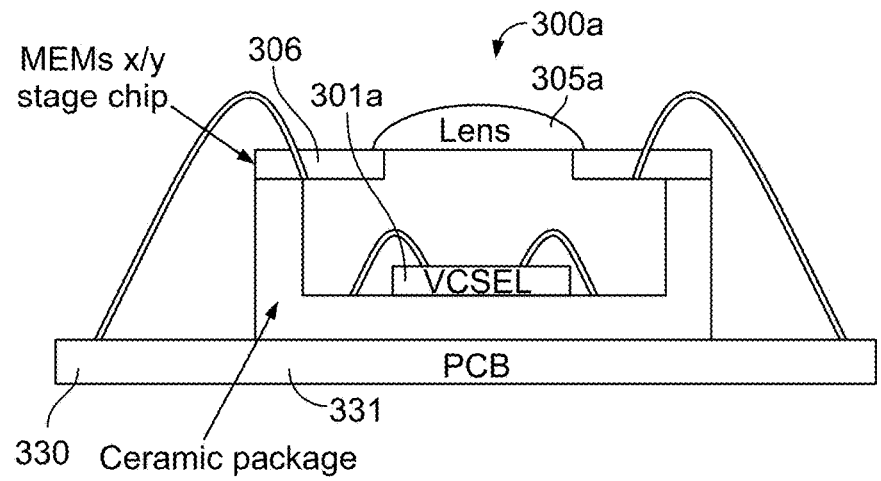
FIGS. 3A-3C show different embodiments of the light control mechanism (LCM) of the present invention.
Figure 3B:
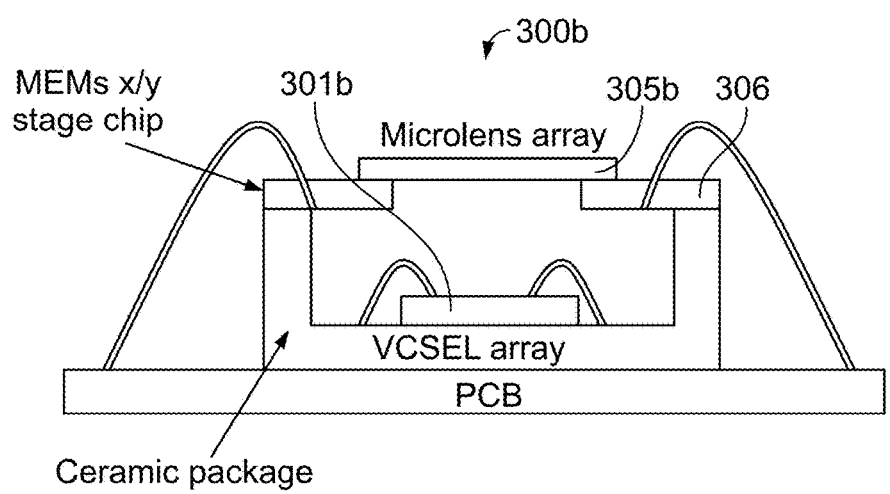

Alternately, in FIG. 3B, an illumination system 300b is shown which is substantially similar to that of 300a, but rather than a single discrete lens 305a, a microlens array 305b is shown. In this case the entire array of lenses is moved as one by the MEMS 301b as shown.

Figure 3C:
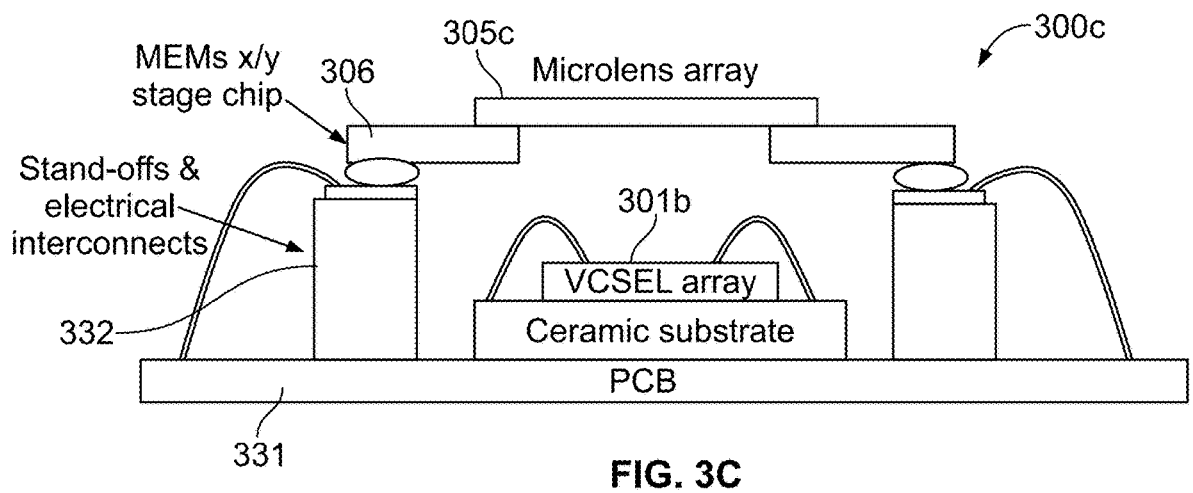
Figure 5A:
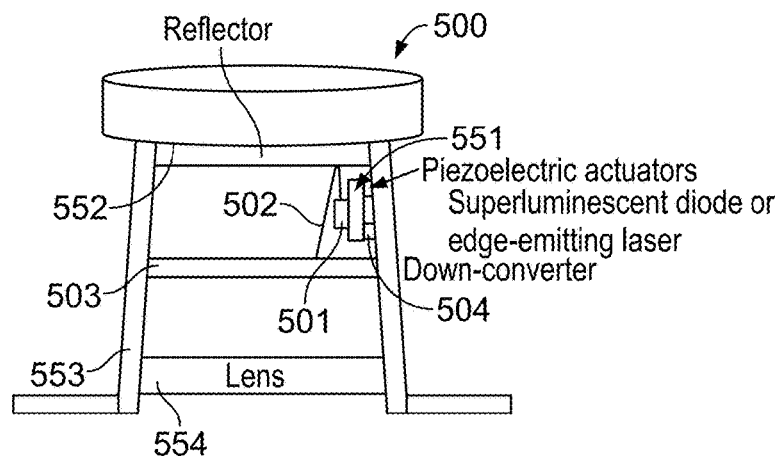
FIG. 5A shows one embodiment of the illumination source of the present invention.
Figure 5B:
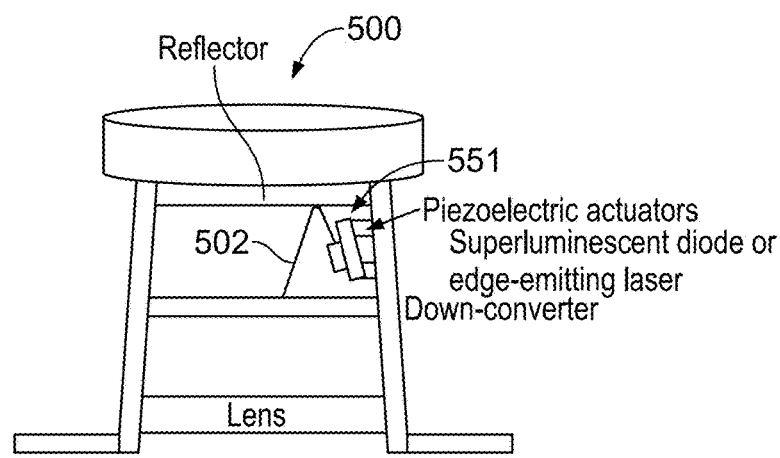
FIG. 5B shows the luminaire FIG. 5A with the coherent beam altered to change the direction of the emitted incoherent light.

In yet another embodiment shown in FIG. 3C, the illumination source 300c is not a ceramic package 331 as shown in FIGS. 3A and 3B, but rather comprises discrete a discrete ceramic substrate upon which the CLED 301c is mounted. The ceramic substrate is mounted to a PCB. On either side of the ceramic substrate are standoffs with electrical interconnects 332. As with the illumination source 300b, illumination source 300c uses a MEMS 306 to move the entire array of lenses 305c as one. Still other embodiments will be obvious to those of skill in the art in light of this disclosure.

Rather than bending the optical path of the coherent light using a lens, in another embodiment, the optical path of the coherent light is altered using a metasurface. Beam steering with metamaterials is known. Metasurfaces can be designed to deflect the laser beam and/or change the beam shape. For example, a metasurface can modify the beam shape for fiber coupling—e.g., multi-lobes can be created, and the beams can be coupled into two different fibers without external optics.

Figure 9:
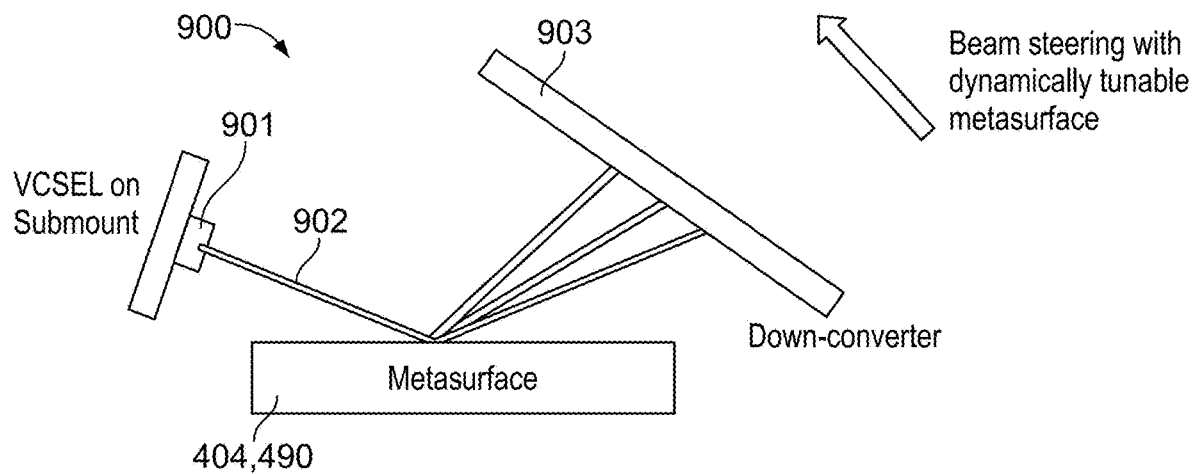
FIG. 9 shows another embodiment of the LCM in which a metasurface is used.

Referring to FIG. 9, one embodiment of the illumination source 900 is shown in which the second optical element of the LCM 904 is at least one controllable metasurface 990, and the actuator changes at least one or more metaatom characteristics of the metasurface to thereby change the direction of the optical path 902 of the coherent light as shown. In the embodiment shown in FIG. 9, the optical path 902 is reflected off of the metasurface 990 at different angles depending upon the characteristics of the metasurface. Here, the coherent light 902 is generated from a surface emitting CLED 901 mounted, for example, on a substrate, and is reflected off of the metasurface 990 and into the optical element 903, which, in this case, happens to be a down-converter.

The angle at which light is reflected off the metasurface depends upon the characteristics of the metasurface. The actuator is configured to change these characteristics to obtain the desired angle of reflection. For example, the actuator may change the size, shape and distance between metaatoms of the metasurface. To this end, the actuator may stimulate the metasurface using at least one of an electric field, an electrostatic force, optical tuning (plasmonics), and/or manipulating optical nonlinearity (Mie resonators). Such stimulation techniques are known. For example, in some LIDAR applications the metasurface is combined with liquid crystals where changing voltage across the metasurface (optical antennas) with liquid crystals changes causes the direction of the beam to change. The same configuration may be used for visible light steering. The phase delay is proportional to the applied voltage which rotates the liquid crystals and shifts the resonant wavelength. Still other means of altering the characteristics of the metasurface will be known to those of skill in the art in light of this disclosure.

Figure 10:
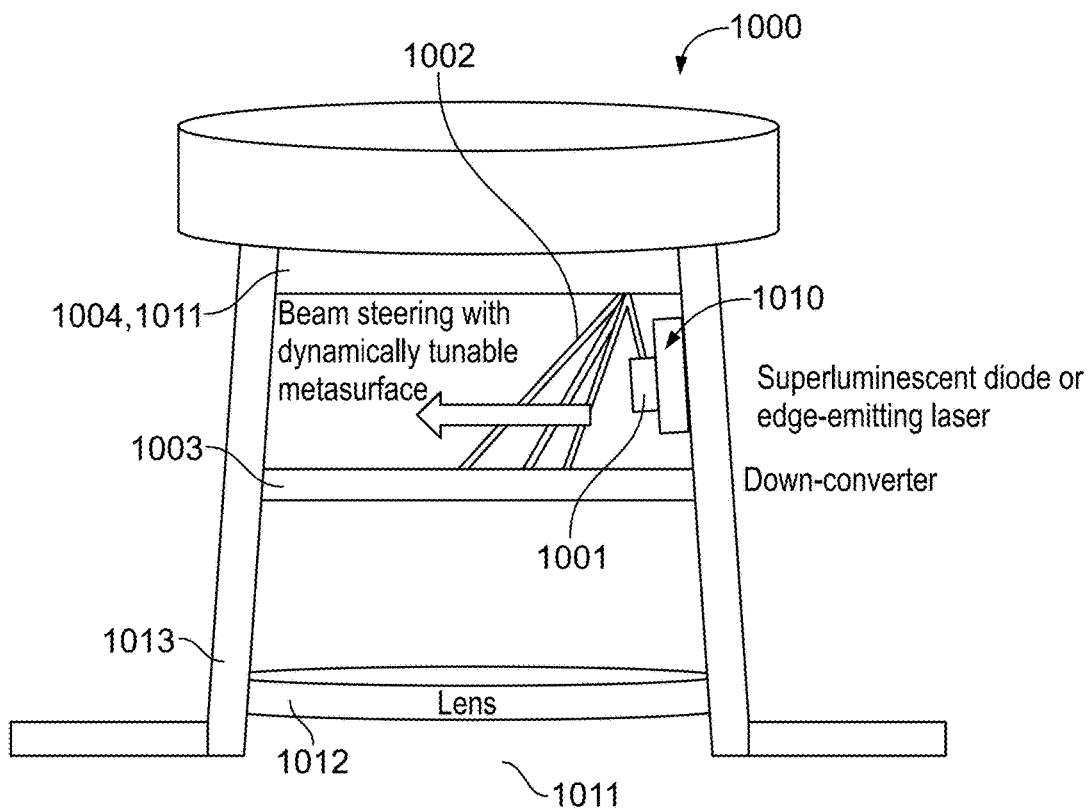
FIG. 10 shows an embodiment of a luminaire comprising a light source using a metasurface to alter the path of the coherent beam to change the emitted incoherent light.

The illumination source 900 may be configured in different ways when packaged in a luminaire. For example, referring to FIG. 10, a luminaire 1000 using one embodiment of the illumination source 1010 of the present invention is shown. In this embodiment, the luminaire 1000 comprises a housing 1003 in which the illumination source 1010 is housed. The illumination source 1010 comprises a CLED 1001, which, in this embodiment, is an edge emitting device. It is configured such that the coherent light being emitted therefrom has an optical path incident upon a second optical element 1004, which, in this embodiment, is a metasurface 1011. Depending upon the characteristics of the metasurface 1011, the coherent light is reflected at various angles. The reflected light is incident upon the optical element 1003 which, in this embodiment, is a down-converter. As mentioned above, by varying the angle of incidence upon the optical element 1003, the incoherent light 1011 emitted therefrom varies as well. In this embodiment, the incoherent light is coupled to a lens 1012 which is configured to shape the incoherent light 1011 emitted from the luminaire 1000. It should be understood that this is just one embodiment of a luminaire of using the illumination source of the present invention. Still other embodiments will be readily apparent to those of skill in the art in light of this disclosure.

In yet another embodiment, the LCM comprises at least one actuator operatively connected to the CLED to move the CLED in response to a control signal, wherein moving the CLED causes the optical path to change such that the incoherent light being emitted from the optical element changes its direction. For example, referring to FIGS. 4A-4F, various embodiments of an LCM for changing the direction of the optical path of the coherent light are shown. Generally speaking, these LCM embodiments differ from the aforementioned embodiments in that, rather than bending or having the optical path reflected as described above, the orientation of the CLED is changed to alter the direction of the optical path of the coherent light.

More specifically, referring to FIGS. 4A and 4B, an embodiment of a light source subassembly 400a is shown. The subassembly 400a comprises a single CLED in a ceramic package 442 and the optical element 403 is a down-converter. This particular embodiment also comprises a lens 405A for shaping the incoherent light 411. The LCM in this embodiment comprises actuators 406, which are configured to move the entire ceramic package 422 to change the direction of the coherent light 402, and thus the incoherent light 411. More specifically, referring to FIG. 4A, the optical subassembly 400a has a neutral state in which the coherent light 402 is being emitted essentially perpendicular to the substrate 450. In FIG. 4B, the actuators 406 are actuated such that the coherent light 402 is emitted from the subassembly at an angle to the substrate, causing the incoherent light 411 to be emitted at an angle to the substrate as well.

Referring to FIGS. 4C and 4D, an embodiment of the optical subassembly 400b, similar to that of FIGS. 4A and 4B, is shown. Like subassembly 400a, subassembly 400b comprises a ceramic package 442 mounted on actuators 406 and a down-converter optical element 403. However, unlike subassembly 400a, subassembly 400b comprises an array of CLEDs and a microlens array 405b. Regardless of the embodiment, actuating the actuators 406 causes the incoherent light 411 to change direction from the neutral state shown in FIG. 4C to the actuated state shown in 4D.

Referring to FIGS. 4D and 4F, yet another embodiment of a subassembly 400c is shown. In this embodiment, a plurality of subassemblies 400b are mounted on a substrate such as a PCB board 444. However, in this embodiment, the actuators 406 are not connected directly to the ceramic package 442 as in the embodiments of FIGS. 4A and 4B, but rather connected to the substrate 444 upon which the subassemblies 400b are mounted. Thus, moving the substrate moves the plurality of subassemblies, causing the incoherent light 411 to change direction from the neutral position as shown in FIG. 4e to the actuated position as shown in 4F.

A variety of different actuators can be used in the embodiments considered above. Although the embodiments disclosed above used either piezoelectric actuators or MEMS, the two approaches may be interchangeable. Additionally, other approaches exist. For example, in yet another embodiment, actuation of the lens or array of lenses is performed manually. For example, the illumination source may have an external lever or screw mechanism which the user can manipulate to affect the position of the lens, and therefore alter the direction/shape of the incoherent light leaving the illumination source. Still other actuation mechanisms will be obvious to those of skill in the art in light of this disclosure.

In yet another embodiment, the LCM comprises at least one second optical element configured to receive at least a portion of the incoherent light, and an actuator operatively connected to the second optical element to change at least one characteristic of the second optical element in response to a control signal, wherein changing the characteristic causes the incoherent light to change its direction. In other words, rather than altering the optical path of the coherent light, in this embodiment, the path of the coherent light is fixed, and the optical path of the incoherent light is changed. For example, referring to FIG. 12, in this embodiment of the illumination source 1200, the LCM 1204 comprises one or more lenses 1205 in the optical path of the incoherent light 1211. The lenses are operatively connected to a MEMS actuator 1206, such that, when moved by actuator 1206, the optical path of the incoherent light 1211 changes. In this respect, the LCM 1204 is similar to the LCM 104 except the LCM 104 alters the optical path of the coherent light, while LCM 1204 alters the optical path of the incoherent light.

Figure 14:
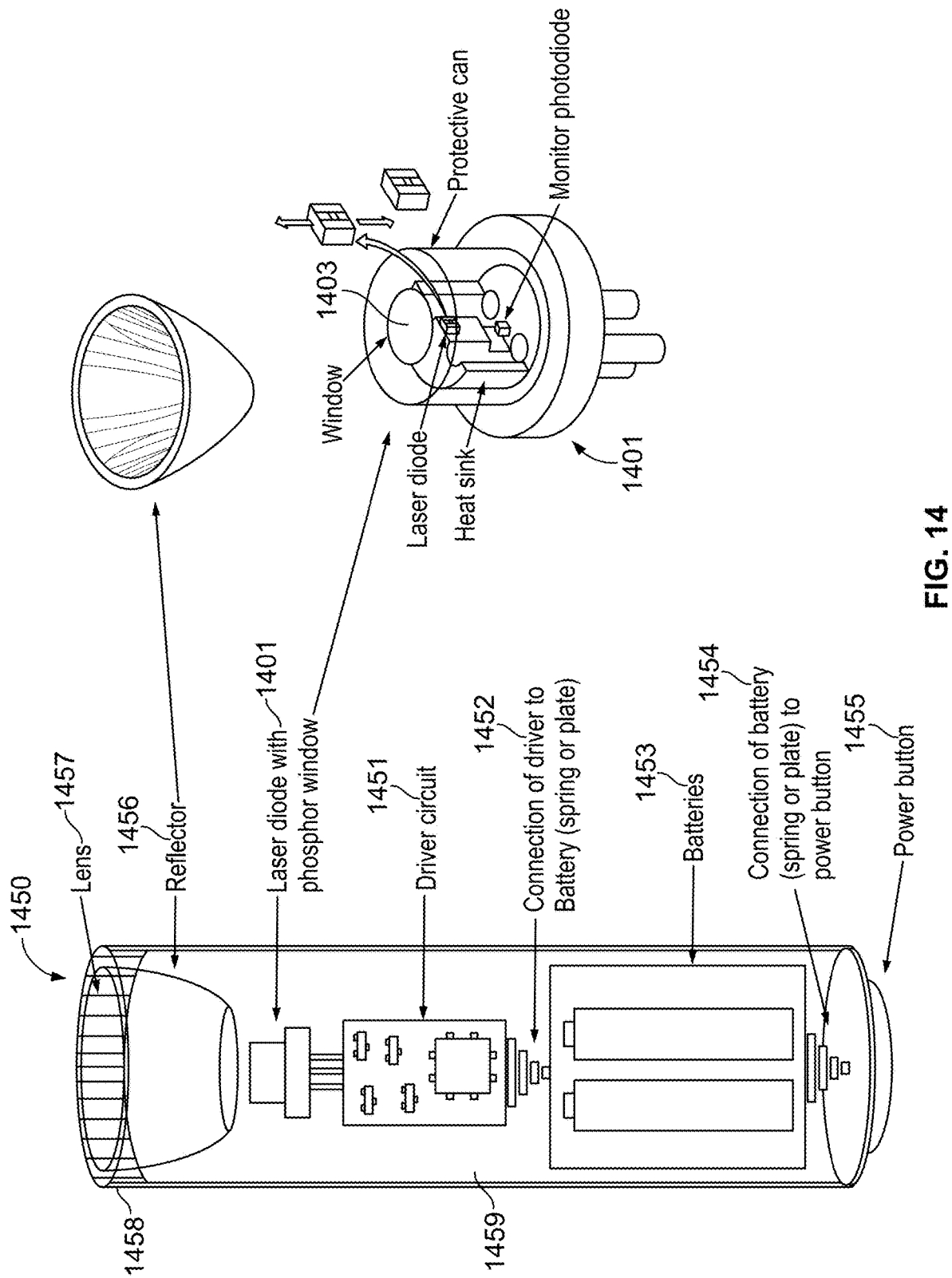
FIG. 14 shows one embodiment of a flashlight having a TO can with the phosphor window.

Another embodiment in which the LEM alters the optical path of the coherent light is shown in FIG. 14. Referring to FIG. 14, a flashlight 1450 is shown comprising one embodiment of illumination source of the present invention. Specifically, the flashlight 1450 comprises a TO can 1402 with the phosphor window 1403 for converting coherent light generated from a laser within the TO can to substantially white light. In this particular embodiment, the flashlight comprises also comprises a driver circuit 1451 for driving the TO can, a connection 1452 to a battery 1463 and a connection 1454 from the battery to a power button 1455. In this embodiment, to shape the light, the LCM modifies the incoherent light using a reflector 1456, lens 1457 and actuator 1458. The actuator is threadably engaged with the housing 1459 of the flashlight 1450 such that, by manually turning the actuator 1458, the lens 1457 and reflector 1456 move axially with respect to the incoherent light, thereby changing the focus/shape of the incoherent light beam.

It should be understood that the LCM embodiments described above are for illustrative purposes only and should not limit the claims. Other LCM embodiments will be obvious to those of skill in the art in light of this disclosure.

CLED

As used herein, the CLED may be one or more solid state devices that emits coherent light along an optical path having an optical axis. In one embodiment, the CLED is at least one of a laser, an array of lasers, a superluminescent diode (SLD), or an array of SLDs. Examples of lasers include, for example, a vertical cavity surface emitting laser (VCSEL), and side emitting lasers, such as a double channel, planar buried heterostructure (DC-PBH), buried crescent (BC), distributed feedback (DFB), or distributed bragg reflector (DBR). In one particular embodiment, the CLED is a VCSEL, which can provide a very small circular spot. Another benefit of a VCSEL is that it emits light in the same orientation as LEDs, making them amenable to surface mount packaging. Edge emitting laser diodes also provide a narrow spot, but their beam is elliptical and is more challenging to integrate in a surface mount configuration. In one particular embodiment, the CLED is a SLD, which combines the directionality typical of laser diodes with the spectral width of LEDs. A SLD reaches amplified spontaneous emission conditions but does not lase (stimulated emission) resulting in a low temporal coherence thus leading to speckle-free illumination seen in edge-emitting lasers.

Figure 11A:
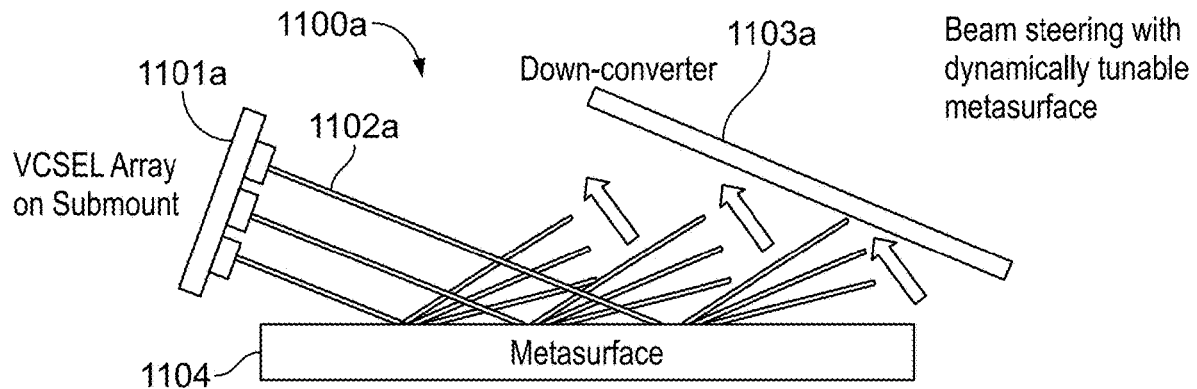
FIG. 11A shows an embodiment of an LCM using a metasurface to change the direction of multiple coherent beams transmitted from an array of CLEDs.
Figure 11B:
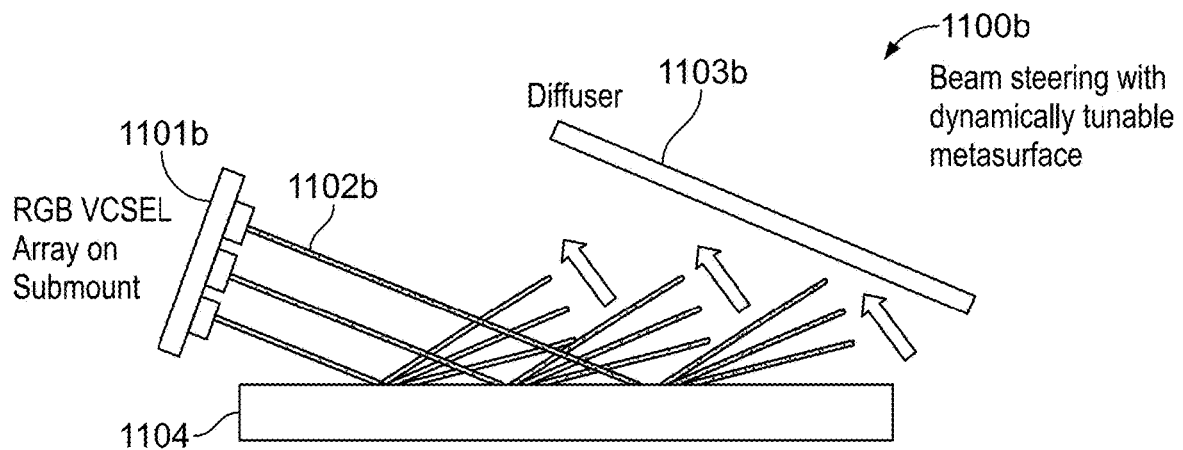
FIG. 11 B is similar to the embodiment of FIG. 11A, except that the CLEDs have different wavelengths.
Figure 12:
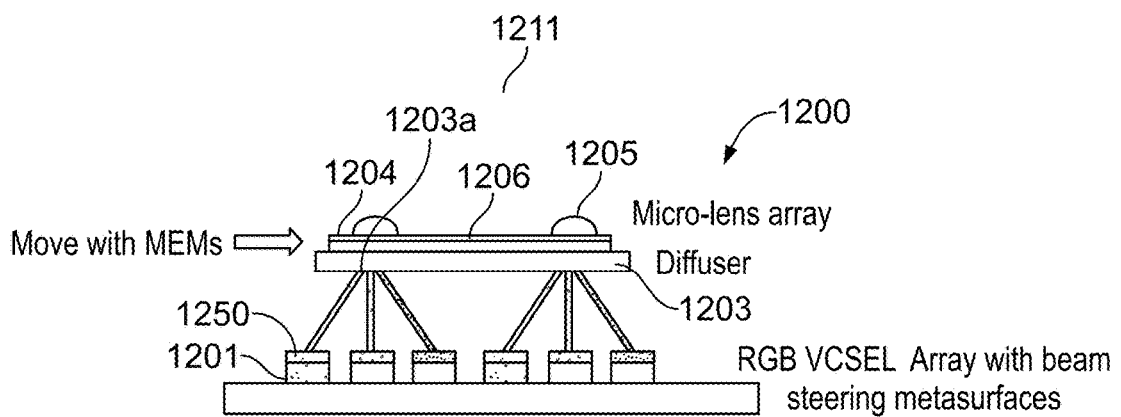
FIG. 12 shows an embodiment of the LCM in which metasurfaces steer coherent beams of different wavelengths to a particular point on a diffuser, and the LCM comprises lenses to alter the direction of the emitted incoherent light.
Figure 13A:
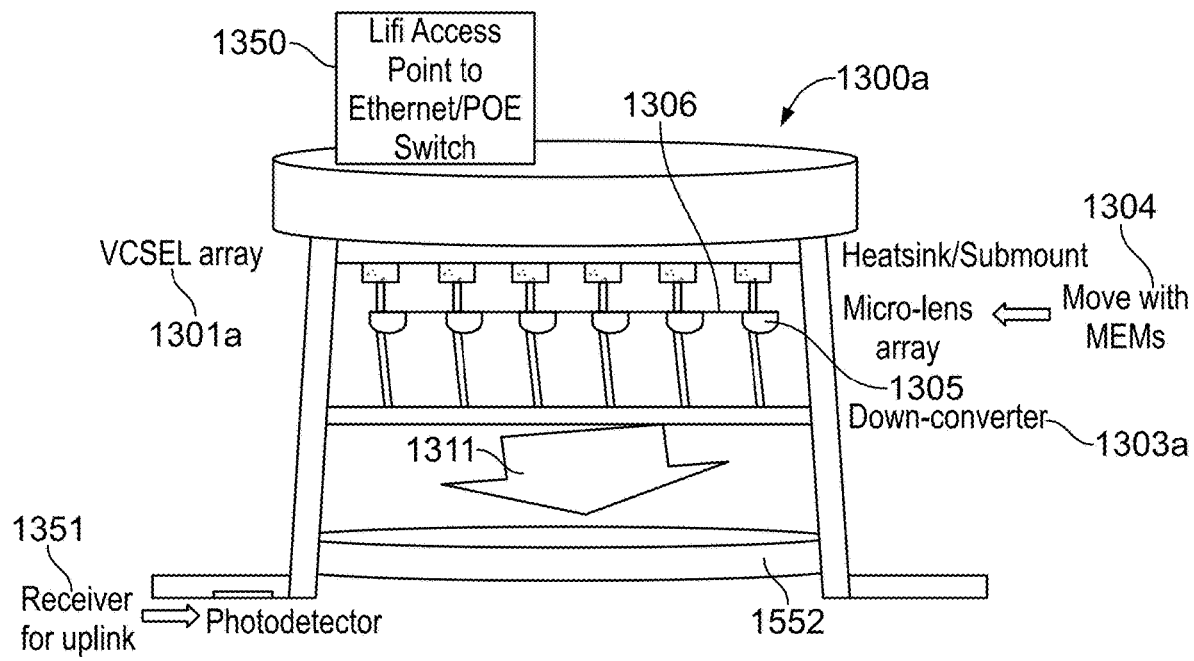
FIGS. 13A-13E show various embodiments of LIFI in luminaires using the different embodiments of the illumination sources described herein.
Figure 13B:
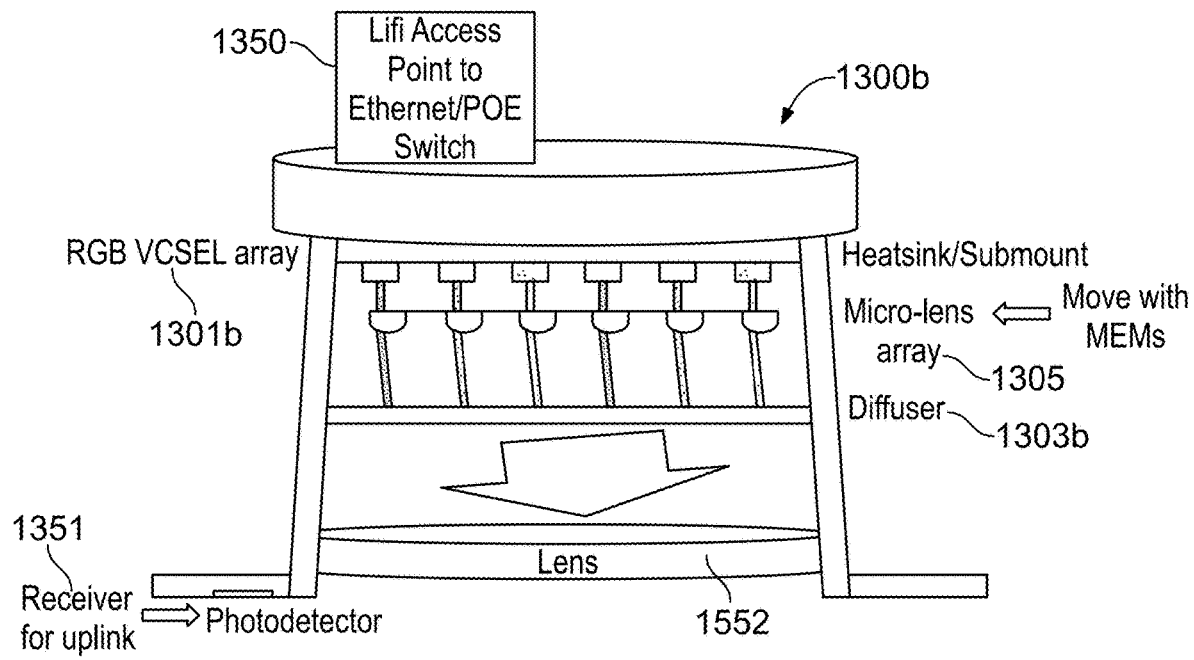
Figure 13C:
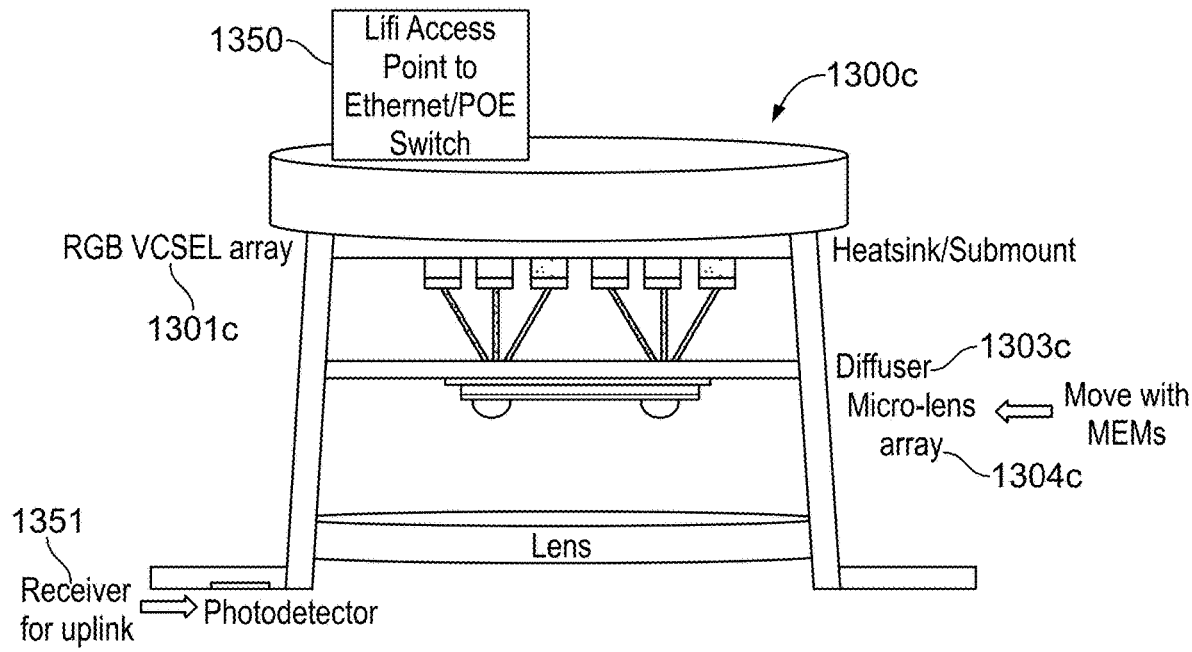
Figure 13D:
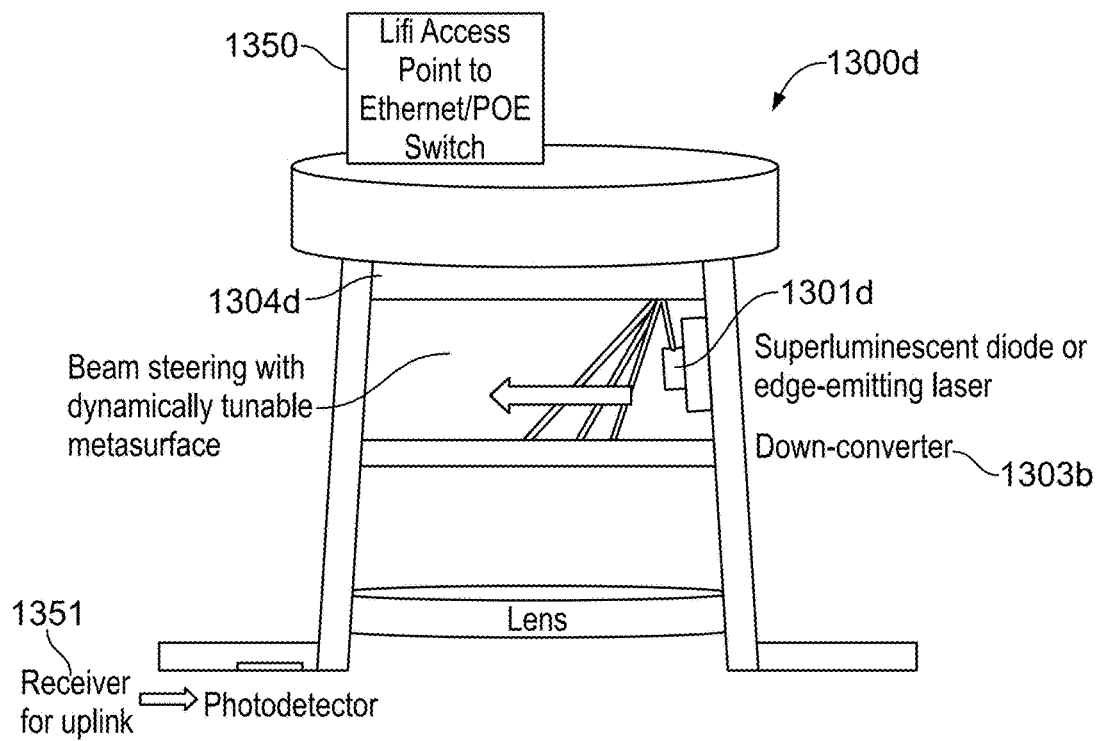
Figure 13E:
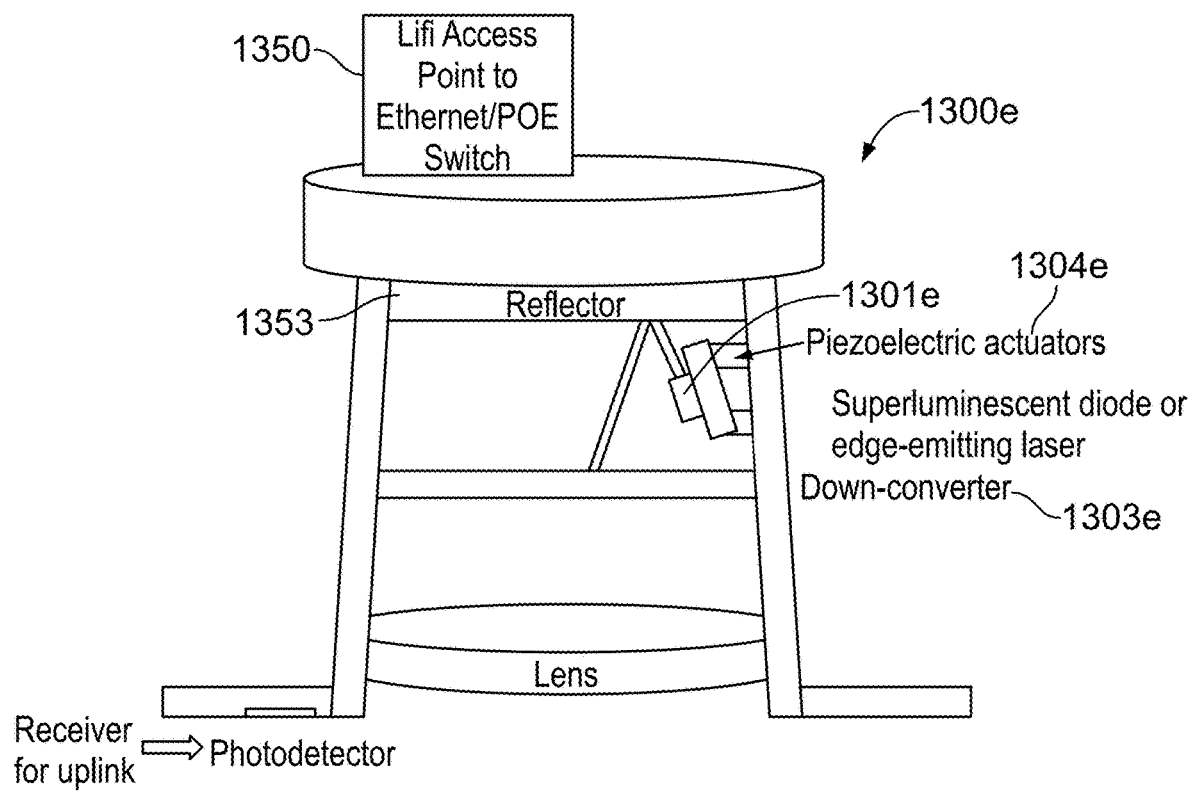

The CLED(s) may be packaged in different ways. For example, in one embodiment, the CLED may be a single discrete device or it may be assembled or integrated as an array of devices. Additionally, the CLED may be discrete chips, an array on a chip, or discrete chips in an array. Moreover, a single package may comprise not only the CLED, but also other elements (e.g., lenses, microlens arrays, down-converters, driver circuits, and LCMs) as described herein. For example, in one embodiment, the CLED(s) may be packaged in a TO can (see FIG. 14), or in ceramic package (see, for example, FIGS. 3A and 3B), or with a metasurface to bend their optical path (see FIGS. 11A and 11B). In one embodiment, the CLEDs are packaged with a metasurface to alter the path of the coherent beam as shown in FIG. 12. Specifically, in this embodiment, RGB CLEDs are integrated with metasurfaces such that the coherent beams from the CLEDs are focused on a point 1203a of a diffuser 1203, thereby combining different color CLEDS into a diffusing lens. This may reduce complexity of combining RGB laser beams that is typically done with mirrors.

In one embodiment, the array of CLEDs comprises CLEDs configured for emitting coherent light having the same wavelength. In embodiments in which multiple CLEDs have the same wavelength, the CLEDs may be formed on a monolithic chip. Additionally, in applications in which multiple CLEDs have the same wavelength, one of more of the CLEDs may function as a pump for a down-converter (described below). Although different pump wavelengths can be used to pump, in one embodiment, the pump light is blue (400-460 nm). Examples of commercially available blue pumps include GaN blue edge emitting laser diodes from Nichia or OSRAM. GaN-based blue VCSELs are also in being developed. GaN blue superluminescent diodes are commercially available by Exalos. Alternatively, in one embodiment, the CLEDs comprise violet (V) and/or ultraviolet (UV) CLEDs which are coupled with a down-converter optical element to convert at least a portion of V and/or UV light to longer wavelengths. In one embodiment, V and/or UV CLEDs are used without a down-converter, for example, for antibacterial applications polymer curing applications.

In one embodiment, the CLEDs are configured in an array in which two or more of the CLEDs are configured for emitting coherent light of different wavelengths. In embodiments were multiple wavelengths are used, the CLEDs of different wavelengths may be formed on different dies. Different dies of multiple wavelengths may then be combined on a submount. Although this may be more expensive than preparing a monolithic chip with an array of CLEDs as mentioned above with respect to singular wavelength embodiments, if the application calls for multiple CLEDS for total optical output, this approach may make more sense.

In one embodiment, the array of CLEDs comprises separately controllable drivers controlled by a control signal such that the output of at least a portion of the array of CLEDs is variable based on the control signal. In one embodiment, the CLED is configured to emit any color, including visible light, such as red (R), green (G), blue (B), and violet (V). For example, referring to FIG. 2, RGB CLEDs 201*a*, 201*b*, and 201*c* are shown. Likewise, FIGS. 11B and 12 show alternative embodiments of using RGB CLEDs. In one embodiment, non-visible wavelength such as ultraviolet (UV) and/ or infrared (IR) CLEDs may be used. In one embodiment, the CLEDs comprises only RGB CLEDs. In one embodiment, the CLEDs comprises RGB CLEDs plus one or more UV, V, and/or IR CLEDs, for example, for full spectrum color and/or circadian rhythm and/or antibacterial applications (as discussed below).

In one embodiment, the illumination source uses a combination of pump CLEDs and non-pump CLED. For example, in one embodiment, blue CLEDs (400-460 nm) are used for pumping, and additional CLEDS, for example, 480 nm, are used to achieve the desired spectrum/quality of light.

As is well known, CLEDs are driven by driver circuitry. This circuitry may be configured in different ways. For example, in one embodiment, one driver may drive multiple CLEDs, and, in another embodiment, each CLED may have a discrete driver circuit. In one embodiment, the driver circuitry is integrated with printed circuit board (PCB) upon which the CLED substrate or package is mounted. Alternatively, the driver circuitry may be integrated in a TO can as is well known. Still other driver circuitry configurations/ packaging will be known to those of skill in the art in light of this disclosure.

Optical Element

The optical element functions to convert coherent light to incoherent light. To this end, the optical element will have different configurations depending on the illumination source configuration and the CLEDs used. For example, in an embodiment, in which the CLEDs have the same wavelength, the optical element may be configured as at least one down-converter for converting at least a portion of the coherent light to converted light having one or more different wavelengths such that the incoherent light is a combination of light having the wavelength and the different wavelengths. The down-converter may be any know material or device for receiving light of one wavelength and emitting light of a different, typically longer, wavelength. Such materials and devices are well-known and include, for example, phosphor, quantum dots, perovskites and/or other materials designed to down convert some, most or all of the energy to a different wavelength. For example, referring to FIGS. 1A & 1B, 5*a* & 5B, 9, 10, and 11A, the optical elements 103, 503, 903, 1003, and 1103*a*, respectively, are down-converters configured to convert a portion of the coherent light beam to light having one or more longer wavelengths. Similarly, referring to FIG. 14, the optical element 1403 comprises a phosphor window incorporated into a TO can 1401 for down converting light. In this embodiment, the typical glass window is replaced with phosphor in glass or ceramic phosphor as the window material. (Typically TO cans use glass lenses (various formulations) or sapphire lens.)

In one embodiment, the down-converter receives the coherent light of one wavelength and converts it to an incoherent white light, which may have different qualities as described below. In some embodiments, the down-converter may convert all of the CLED coherent light or just a portion of the CLED coherent light, allowing the remaining portion to leak in the emission of the illumination source. Applications will dictate whether to leak certain wavelengths to attain, for example, full-spectrum color, defined ultraviolet and/or violet peaks for antibacterial purposes, or increase or decrease blue peaks for circadian regulation as discussed below in greater detail. Again, one of skill in the art will understand how to configure the spectrum to achieve the desired result in light of this disclosure.

Figure 7:
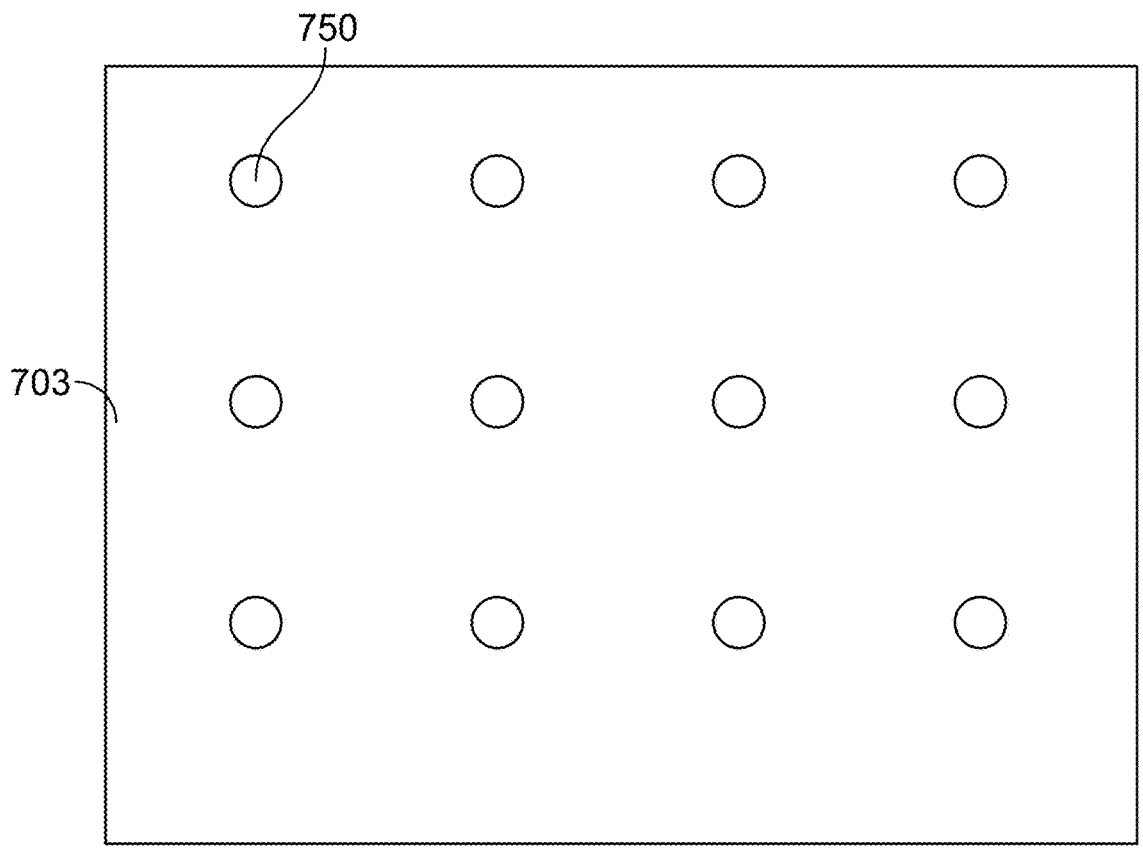
FIG. 7 shows one embodiment of an array of phosphors.

The down converting may be configured in different ways. For example, in one embodiment, the down converting optical element is configured as a single element such as the optical element 403 in FIG. 4A. Alternatively, in another embodiment, it may be configured as an array of elements 703 as shown in FIG. 7. In this particular embodiment, a glass plate with phosphor sections 750 may be aligned along the optical path of the coherent light from the CLEDs. For example, referring to FIG. 8, an aligned view of the CLEDs, MEMS 606, and phosphor array 705 is shown with drivers on a PCB.

In one embodiment, the optical element is a diffuser for combining the coherent light having different wavelengths such that the incoherent light is a combination of light having the different wavelengths. In other words, in an embodiment in which CLEDs of different wavelength are used, the optical element need not necessarily be a down-converter, and may be instead a diffuser to combine the different wavelengths of coherent light into an incoherent emission light. Diffusers are well-known and will not be discussed herein in detail. Suffice to say that a diffuser is typically configured to mix the various coherent light sources evenly to generate a homogeneous incoherent emission. For example, referring to FIGS. 2, 11B and 12, the optical elements 203, 1103*b*, 1203, respectively, are diffusers for combining the different coherent emissions from RBG CLEDs.

It should be understood that when configuring the down-converter, thermal management of down-conversion media under high optical flux density should be addressed. For example, in one embodiment, the down-converters are heat sunk. In one embodiment, thermally conductive media (e.g. thermally conductive glass) surrounds the phosphor to remove the heat from the down-conversion process. Alternatively, in one embodiment, a single crystal ceramic phosphor is used to improve the thermal performance. Alternatively, the laser beams from an array of CLEDs can help spread the optical density load on the phosphor.

Although the embodiments illustrated herein show the down-converter downstream of the LCM lenses along the optical path of the coherent light, alternatively, they may be upstream of the LCM lenses. In one embodiment, an illumination source having a piezoelectric actuator is configured with the down-converter disposed upstream of the LCM lens(es) along the optical path of the coherent light.

The various embodiments of the LCM, CLED(s), and optical element disclosed herein can be mixed and matched in different combinations/permutations to form illumination sources other than those described herein. Such permutations of the LCM, CLED and optical element will be obvious to those of skill he art in light of this disclosure.

Spectrum

The emitted incoherent light may be configured to suit the application. For example, in some applications full-spectrum white light may be desired, in others, moderation of circadian cycles may be the objective, and it still other applications antimicrobial light may be the goal. More specifically, systems according to the principles of the present disclosure may be arranged to produce a spectrum tailored to provide disinfection (e.g. a spectrum that includes violet and/or UV), healthy lighting (e.g. a spectrum that effects circadian rhythms of those exposed to the spectrum), full spectrum lighting (e.g. a spectrum that has energy in most or all of the visible spectrum), a narrow band of light (e.g. a spectrum with energy in the UV, visible and/or the infrared), and/or several narrow bands of light, etc.

In one embodiment, the combination of light from the array of CLEDs is white light. In embodiments designed to be full spectrum, which may or may not include disinfection light and/or circadian effective light, the spectrum is configured for acceptable color temperature with high CRI and high lumens per watt. For example, the CLEDs, with and/or without phosphors, may be arranged to produce energy throughout all or most of the visible spectrum to produce a color temperature between 2700 and 6000K, or higher (e.g. 10,000 k) with a CRI of greater than 80, 90, or more. In one embodiment, the white light has a correlated color temperature of between 2700 k and 10000 k and a color rendering index of over 80.

Applications for full-spectrum white light include not only residential and commercial lighting applications, but also medical device applications in which the light source is coupled to an optical fiber such as laparoscopy, endoscopy, laryngology, etc. In this respect, currently xenon light sources or LED based light sources are used for fiber lighting in minimally invasive surgical procedures. However, the optical coupling of a coherent light-based illumination source is better than LED/xenon light sources.

In one embodiment, the combination of light from the array of CLEDs includes a violet component sufficient to have an antibacterial effect. In another embodiment, the combination of light includes a UV component sufficient to have an antibacterial effect. In one embodiment, the combination of light has a spectral power distribution (SPD), wherein the power of the violet portion of the SPD is at least 25%, at least 30%, at least 35% or at least 40% of the overall power of the SPD. In one embodiment, the violet component comprises a peak wavelength of at least one of 395 nm or 405 nm. In embodiments including violet light, the violet light may be within the energy range of 380 to 420 nm. The violet light may be continuous (e.g. using a violet or ultra-violet CLED with a down conversion material) within the range or discontinuous (e.g. using a violet CLED without using a down conversion material), it may fill the range, or it may not fill the range. For example, the violet may include a CLED that produces light around 405 nm and pump a phosphor such that there is a narrow band at 405 nm and a continuous spectrum at longer wavelengths. A 405 nm CLED may not pump a phosphor such that the energy does not get down converted and remains coherent or is made non-coherent by projecting the energy through another structure. A 405 nm CLED may not pump a phosphor but it may be converted into an incoherent beam. 405 nm is just one example. The violet may be generated by other CLEDs, such as 395 nm or shorter or longer, 410 nm or shorter or longer, etc. The violet may also result from a combination of CLEDs within the violet range (e.g. a combination of 395 with and/or without phosphor and 405 nm with and/or without phosphor). Each CLED may be controllable such that color mixing ratios and light intensities can be adjusted in a dynamic or static fashion.

In one embodiment, the combination of light includes energy within a melanopic curve adapted to affect circadian rhythms of a person exposed to the combination of light. In one embodiment, the energy within the melanopic curve is controllable between high and low energy based on the control signal. In embodiments designed to affect a person's circadian rhythms, the light may be tailored to produce energy maximized to a melanopic curve. The curve spectrum is generally described by a normally distributed curve between 400 and 600 nm (e.g. with most effectiveness between 450 and 525 nm), as compared to the normally distributed photopic curve between 380 and 800 nm. It should be understood that the melanopic curve may or may not be normally distributed and the general energy range may change as more is learned about a person's response to circadian effective lighting. A system designed to effect a person's circadian rhythms may also provide dynamic or controllable light levels within the effective range. For example, at night, when a person is trying to wind down and go to sleep the energy delivered in the melanopic range could be reduced so as to encourage the body to release melatonin. If the person is trying to wake, energize or stay alert, the energy delivered in the melanopic range could be high to suppress melatonin production. Such a system may have a CLED arranged to pump a phosphor to generate, for example, a broadband cyan color and this CLEDs energy may be controlled to deliver the correct amount of melanopic energy for the situation.

LiFi

In one embodiment, the illumination source of the present invention is integrated with LiFi. LiFi is high speed bidirectional network for the wireless communication of data using light. LiFi is generally considered a two-way data communication, whereas visual light communication (VLC) tends to be a one-way communication. In this embodiment, the illumination source is configured to communicate data wirelessly (i.e. in a downlink channel) by emitting modulated light from a luminaire. Specifically, the coherent light is modulated such the light emitted from the luminaire communicates data. This modulation of coherent light is however imperceptible to the human eye. In one embodiment, the receiver of the emitted modulated light (e.g. a laptop computer, smart phone, etc.) is configured to communicate data wirelessly to the luminaire (i.e. the uplink channel). In one embodiment, the uplink communication uses nonvisible light (e.g. IR light).

FIGS. 13A-13E show various embodiments of LiFi being integrated into a luminaires having illumination sources of the present invention. For example, referring to FIG. 13A, luminaire 1300a comprises a plurality of CLEDs 1301a mounted to a heatsink/sub mount for emitting coherent light along the pathway, an array of lenses 1305 in the pathway, and an LCM 1304 comprising a microlens array 1305 in the optical pathway of the coherent light and an actuator 1306 for moving the microlens array 1305. The optical element in this embodiment is a down-converter 1303a. In this particular embodiment, the luminaire 1300a also comprises a LiFi access point to ethernet/POE switch, and, optionally, a receiver for uplink 1351.

In one embodiment, the illumination source is used for the downlink connection by modulating the coherent light. In one embodiment, the incoherent light it is modulated. In one embodiment, a luminaire is configured with a nonvisible light receiver for receiving the uplink data.

In one embodiment, CLEDs of different wavelengths are discretely modulated to facilitate the use of wavelength division multiplexing (WDM) to enhance LiFi speeds compared to, for example, a single channel LiFi with a blue CLED. For example, in one embodiment, the multiple wavelength CLEDs comprise an RBG array. The individual wavelength CLEDs may be discretely modulated to communicate different signals, but, when combined, form white light. Additional CLED colors can be added to not only improve the color rendering index (CRI) but add additional channels for WDM purposes—e.g. amber and/or cyan CLEDs may be added. In one embodiment, pump CLEDs (e.g. blue CLEDS) having slightly different wavelengths (e.g. 430 nm, 440 nm, 450 nm) may be separately modulated to communicate different signals, yet each functions to pump a common down-converter.

The other embodiments shown in FIGS. 13 B-F are similar to 413a although may comprise different configurations of CLEDs, different LRMs and different optical elements as described herein.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. An illumination source, comprising:
   at least one coherent light emitting device (CLED) configured for emitting coherent light having an optical path;
   at least one optical element in said optical path for converting at least a portion of said coherent light to incoherent light, said optical element being configured to emit said incoherent light in a direction; and
   a light control mechanism (LCM) for altering said direction of said incoherent light;
   wherein said LCM comprises at least one second optical element configured to receive at least a portion of said incoherent light, and an actuator operatively connected to said second optical element to change at least one characteristic of said second optical element in response to a control signal, wherein changing said characteristic causes said incoherent light to change said direction.

2. The illumination source of claim 1, wherein said second optical element is at least one lens and wherein said actuator changes a position characteristic of said lens relative said optical element.

3. The illumination source of claim 1, wherein said CLED is an array of CLEDs and wherein said array of CLEDs comprises two or more CLEDs configured for emitting coherent light having different wavelengths.

4. The illumination source of claim 1, wherein said actuator comprises a microelectromechanical system (MEMS) positioning system.

5. The illumination source of claim 1, wherein said second optical element is at least one controllable metasurface, and wherein said actuator changes at least one or more metaatom characteristics of said metasurface.

6. The illumination source of claim 5, wherein said metaatom characteristics comprise at least one of size, shape and distance between metaatoms.

* * * * *